United States Patent [19]

Norton

[11] 4,104,279
[45] Aug. 1, 1978

[54] PROCESS FOR N-AROYLIMIDES

[75] Inventor: Richard S. Norton, Wilmington, Del.

[73] Assignee: Suntech, Inc., Wayne, Pa.

[21] Appl. No.: 731,273

[22] Filed: Oct. 12, 1976

[51] Int. Cl.$^2$ ............................................. C07D 209/34
[52] U.S. Cl. ........................... 260/326 N; 260/326 A;
260/326 C; 528/228
[58] Field of Search ........... 260/326 A, 326 N, 326 C

[56] References Cited

U.S. PATENT DOCUMENTS

| 3,890,274 | 6/1975 | D'Alelio ................. 260/326 C X |
| 4,001,179 | 1/1977 | Richter et al. ................. 260/326 N |

FOREIGN PATENT DOCUMENTS 2,025,898  12/1971  Fed. Rep. of Germany ....... 260/326 C

*Primary Examiner*—Ethel G. Love
*Attorney, Agent, or Firm*—J. Edward Hess; Donald R. Johnson; Paul Lipsitz

[57] ABSTRACT

A process for making an N-aroyl derivative of an aromatic imide which comprises reacting an aromatic o-dicarboxylic acid anhydride with a nitrile at a temperature of at least about 250° C and in the presence of a labile proton source.

13 Claims, No Drawings

PROCESS FOR N-AROYLIMIDES

It is known in the art to prepare N-aroyl derivatives of imides by several reactions. For example, N-benzoyl phthalimide was prepared by the reaction of benzoyl chloride with phthalimide (A. T. Titherley and W. C. Hicks, J. Chem. Soc. 89,708 (1906)) in accord with the following scheme:

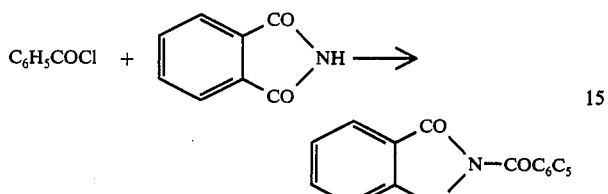

The N-benzyl imide has also been prepared by reaction of benzoyl chloride with the N-lithio derivative of phthalimide (E. M. Kaiser, H. H. Yun, J. Org. Chem., 35,1348 (1970)). As is evident, these reactions require the prior formation of an imide ring structure and such imides are usually derived from the corresponding o-dicarboxylic acid by a previous step.

Titherly and Hicks in the above mentioned references have also shown the conversion of phthalic anhydride to the N-aroyl compound by use of sodium benzamide:

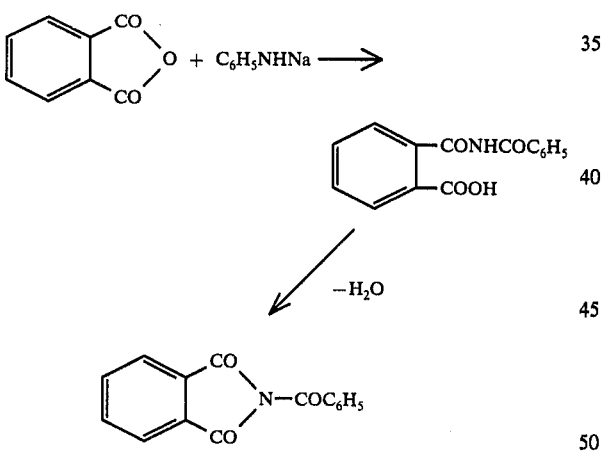

It has now been found, however, that the N-aroyl imide can be obtained directly from the o-dicarboxylic acid anhydride without making the intermediate imide. This is accomplished in accord with this invention by reacting an aromatic o-dicarboxylic acid anhydride with a nitrile at a temperature of at least about 250° C and in the presence of a labile proton source. While not wishing to be bound by the following speculation, it is believed that the reaction involves the following reaction mechanism to explain the catalytic effect of ($H_3O^+$):

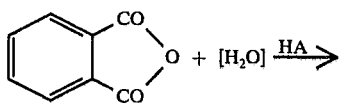

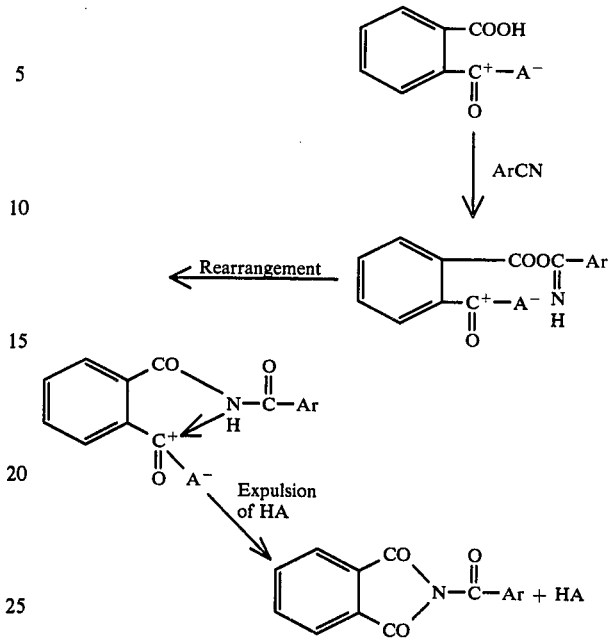

Surprisingly, the reaction requires the use of the dicarboxylic acid anhydride. If the free acid is used, the reaction proceeds in a different manner giving the imide and aromatic acid. Thus, with the free acid the reaction is:

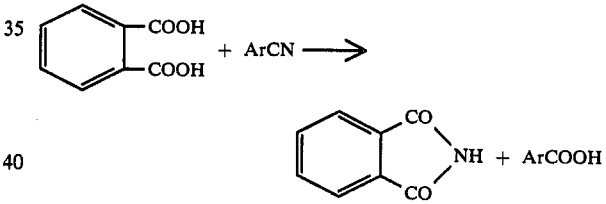

The labile proton source, shown above as HA (e.g. an acid) should only be present in trace amounts and effective proton sources will include water, the strong mineral acids (e.g. HCl, $H_2SO_4$, $H_3PO_4$ etc.) organic acids such as acetic, propionic, and aromatic sulfonic acids and the like. Occasionally the acid used will promote trimerization of the nitrile (i.e. phenyl nitrile yield triphenyl triazine with chlorosulfonic acid) and therefore polyphosphoric acid is preferably used to minimize trimerization and degradation that chlorosulfonic and sulfonic acids tend to cause.

The reaction is quite general and may be applied to a wide variety of anhydrides and nitriles. The aromatic anhydride may be of the benzene, napthalene and anthracene series and even more complex aromatic moieties may be used. Also, dianhydrides may be used. In fact, any thermally stable aromatic anhydride is operable and the method provides a general means for making N-aroyl aromatic imides. Preferred anhydrides will be phthalic anhydride, the anhydrides of 2,3- and 1,8-naphthalene dicarboxylic acids, pyromellitic dianhydride, and 3,3',4,4'-benzophenone tetracarboxylic dianhydride.

Any thermally stable nitrile lacking α-hydrogen atoms is operable in the process. Preferably aliphatic and aromatic mono and polynitiles will be used of structure $R—(CN)_n$ where R is an organic group containing from one to thirty carbon atoms having no free α-hydrogens to the nitrile group and $n$ is an integer of from one to two. Typical examples of preferred nitriles are trifluoroacetonitrile, o, m, or p-tolunitrile, benzonitrile, terephthalonitrile, isophthalonitrile, 2,6-dicyanonphthalene, 2-cyanopyridine, 4,4'-dicyanobiphenyl. Aromatic mono and dinitriles of the benzene and naphthalene series are most preferred.

It will also be understood that substituents may be on the nitrile reactant as long as they are inert to the reaction conditions. Thus, alkyl, alkoxy, nitro, halo, aryl, fluoro and heterocyclic groups such as pyraxole and imide groups may be present.

It will also be understood that where 2 moles of a mononitrile per mole of dianhydride is used, a bis compound is formed and where a dianhydride and a dinitrile are used polymeric compounds can be obtained. Also it will be recognized that the process is of value in cross-linking polyimide resin systems which contain unreacted anhydride groups; the resin and nitrile are mixed and heated under pressure at reaction conditions for crosslinking to occur.

The reaction proceeds readily at temperatures of at least about 250° C up to just below the decomposition temperature of the reactants and products. The general process for the reaction simply involves intimate mixing of the reactants with a catalytic quantity of the proton source and heating to a temperature of at least 250° C for a time sufficient to complete the reaction. When a polyimide resin is used a solvent is helpful to aid in mixing and cresols are useful solvents for this purpose. As the temperature is increased the reactants diffuse and reaction occurs. After cooling the reaction mass the desired product is separated by the usual crystallization techniques of organic chemistry or in the case of polymers the fabricated composite article is ready for use.

EXAMPLE 1

Benzonitrile (10.1g) is mixed with phthalic anhydride (2.0g) in a glass Carius tube and three drops of phosphoric acid are added. The tube is sealed and heated at 300° C for 18 hrs. After cooling, crystal growth occurs at the bottom of the tube in the liquid layer. The material is filtered and the crystals are extracted with petroleum ether. The ether is distilled followed by benzonitrile leaving a crystalline residue in the flask. The crystals are twice recrystallized from methanol (Mp. 175°–178° C) and are characterized as pure N-benzoyl phthalimide (2.1g).

Anal. Calc. for $C_{15}H_9N_1O_3$:C, 71.7%; H, 3.58%; N, 5.57%. Found: C, 71.4%; H, 3.71%, N, 5.51% Infra-red analysis of the compound shows a match for the known compound.

EXAMPLE 2

Terephthalonitrile (6.4g) is mixed with phthalic anhydride (14.8g) in the presence of 3 drops of water and heated at 300° C for 18 hrs. After cooling to room temperature and recrystallization of fractions from petroleum ether, methanol, benzene and acetone there is isolated the triazine of terephthalonitrile (0.4g) and the terephthaloyl bis-phthalimide (4.6g) as identified by comparison of I.R. and CHN analysis and with the properties given in U.S. Pat. No. 2,558,675.

EXAMPLES 3–4

When Example 2 is repeated but acetic acid is used instead of water, a slightly lower yield of the bis-phthalimide is obtained.

Sulfuric acid instead of the water of Example 2 likewise causes a slight decrease in yield and a darkening of the product.

EXAMPLE 5

Example 2 is repeated with isophthalonitrile instead of phthalonitrile. Crystalline product is recovered which is shown by infrared and CHN analysis to be the bis-phthalimide compound.

Similar results are obtained when phosphoric acid and sulfuric acid are used as the proton source.

EXAMPLE 6

2,6-Dicyano naphthalene (1.3g) is reacted with phthalic anhydride (1.57g) for 18 hrs at 300° C in a sealed tube in the presence of 1 drop of $H_3PO_4$. The product is found to be 2-cyanonaphthaloyl-6-phthalimide of the structure:

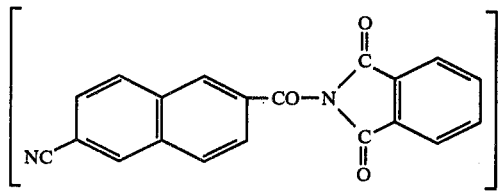

EXAMPLE 7

3,3',4,4'-Benzophenone tetracarboxylic acid dianhydride (4.1g) is reacted with terephthalonitrile (2.0g) in a sealed tube for 18 hrs at 280° C in the presence of a trace of polyphosphonic acid. The product isolated is consistant with the polymeric structure:

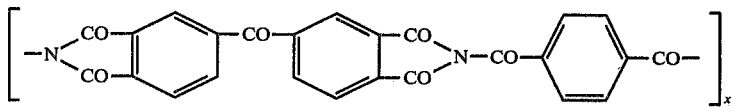

The invention claimed is:

1. A process for making an N-aroyl derivative of an aromatic imide which comprises reacting an aromatic o-dicarboxylic acid anhydride with a nitrile selected from the group of aliphatic and aromatic mono and polynitriles of structure $R—(CN)_n$ where R is the aliphatic or aromatic group containing from one to thirty carbon atoms having no α-hydrogen atom, said aromatic group being of the benzene or naphthalene series and $n$ is an integer of from one to two at a temperature of at least about 250° C and in the presence of an acid as a labile proton source.

2. The process of claim 1 where the nitrile is an aromatic nitrile.

3. The process of claim 1 where the nitrile is an aromatic dinitrile.

4. The process of claim 1 where the anhydride is a dianhydride.

5. The process of claim 1 where the nitrile is terephthalonitrile.

6. The process of claim 1 where the anhydride is phthalic anhydride.

7. The process of claim 1 where the anhydride is pyromellitic dianhydride.

8. The process of claim 1 where the anhydride is 3,3',4,4' benzophenone tetracarboxylic acid.

9. The process of claim 1 where the nitrile is isophthalonitrile.

10. The process of claim 9 where the anhydride is phthalic anhydride.

11. The process of claim 1 where the aromatic nitrile is 2,6-dicyanonaphthalene.

12. The process of claim 1 where the proton source is water.

13. The process of claim 1 where the proton source is polyphosphoric acid.

* * * * *